United States Patent [19]
Caplan et al.

[11] Patent Number: 5,226,914
[45] Date of Patent: Jul. 13, 1993

[54] METHOD FOR TREATING CONNECTIVE TISSUE DISORDERS

[76] Inventors: Arnold I. Caplan, 1300 Oakridge Dr., Cleveland Heights, Ohio 44121; Stephen E. Haynesworth, 3643 Antisdale Rd., Cleveland Heights, Ohio 44118

[21] Appl. No.: 614,912

[22] Filed: Nov. 16, 1990

[51] Int. Cl.$^5$ .......................... A61F 2/28; A61K 35/12
[52] U.S. Cl. .......................................... 623/16; 623/11; 623/66; 424/577; 424/93 U; 424/93 V; 424/549; 530/838; 530/840
[58] Field of Search ................. 623/11, 12, 16, 18, 623/66; 424/422, 423, 95; 435/240.243, 240.2; 530/838, 840

[56] References Cited

U.S. PATENT DOCUMENTS

| | | | |
|---|---|---|---|
| 3,968,567 | 7/1976 | Nevins | 623/66 |
| 4,430,760 | 2/1984 | Smestad | 623/16 |
| 4,596,574 | 6/1986 | Urist | 623/16 |
| 4,609,551 | 9/1986 | Caplan et al. | 623/16 |
| 4,622,120 | 2/1987 | Nevo et al. | 623/16 |
| 4,846,835 | 7/1989 | Grande | 623/16 |
| 4,904,259 | 2/1990 | Itay | 623/66 |
| 5,011,495 | 4/1991 | Hollinger | 623/16 |
| 5,061,286 | 10/1991 | Lyle | 623/66 |

Primary Examiner—Randall L. Green
Assistant Examiner—Debra S. Brittingham
Attorney, Agent, or Firm—Fay, Sharpe, Beall, Fagan, Minnich & McKee

[57] ABSTRACT

The present invention is directed to various processes and devices for utilizing isolated and culturally expanded marrow-derived mesenchymal cells (i.e. mesenchymal stem cells) for treating skeletal and other connective tissue disorders.

23 Claims, 4 Drawing Sheets

METHOD FOR TREATING CONNECTIVE TISSUE DISORDERS

BACKGROUND OF THE INVENTION

The present invention is directed to various methods and devices for treating skeletal and other connective tissue disorders. The methods and devices of the invention utilize isolated and culturally expanded marrow-derived mesenchymal cells which, under certain conditions, can be induced to differentiate into different types of desired connective tissue, such as into bone or cartilage forming cells.

Marrow-derived mesenchymal cells are the formative pluripotential blast cells found in the bone that are believed to be capable of differentiating into any of the specific types of connective tissues (i.e. the tissues of the body that support the specialized elements; particularly adipose, areolar, osseous, cartilaginous, elastic, and fibrous connective tissues) depending upon various environmental influences. Although these cells are normally present at very low frequencies in bone marrow, the inventors of the instant invention have discovered a process for isolating, purifying, and greatly replicating the marrow-derived mesenchymal cells in culture, i.e. in vitro. This discovery is the subject matter of a co-pending U.S. patent application.

In addition to this discovery, the inventors have also discovered that certain factors, such as mechanical, cellular, and biochemical stimuli can be utilized in order to induce differentiation of the culturally expanded marrow-derived mesenchymal cells (i.e. mesenchymal stem cells) into specific types of desired connective tissue such as bone forming cells, etc. As a result, the present invention is directed to methods of utilizing the culturally expanded marrow-derived mesenchymal cells for correcting or modifying connective tissue disorders, such as the regeneration of missing or damaged skeletal tissue, enhancing the implantation of various plastic or metal prosthetic devices through the attachment of the isolated and culturally expanded marrow-derived mesenchymal cells onto the porous surfaces of the prosthetic devices, which, upon the activation and subsequent differentiation of the marrow-derived mesenchymal cells, produce natural osseous bridges.

In addition, the present invention relates to various methods and devices for utilizing the culturally expanded marrow-derived mesenchymal cells in order to enhance hemopoietic cell production. In this regard, one embodiment of the invention is directed to methods for using composite grafts of cultured marrow-derived mesenchymal cells to augment the rate of hemopoietic cell reserve during bone marrow transplantation. An additional embodiment of the invention concerns various methods for using composite grafts of cultured marrow-derived mesenchymal cells and ceramics implanted into hosts, such as into subcutaneous sites in nude mice, as catalysts for the production of a reservoir of hemopoietic stem cells.

SUMMARY OF THE INVENTION

In one aspect, the present invention relates to a method for repairing connective tissue damage. The method comprises the steps of providing culturally expanded purified marrow-derived mesenchymal cells, and applying the culturally expanded purified marrow-derived mesenchymal cells to an area of connective tissue damage under conditions suitable for differentiating the cells into the type of connective tissue necessary for repair.

In a further aspect, the present invention is directed to a method for enhancing the implantation of a prosthetic device into skeletal tissue. The method comprises the steps of providing culturally expanded purified marrow-derived mesenchymal cells, adhering the culturally expanded mesenchymal cells onto the connective surface of a prosthetic device, and implanting the prosthetic device containing the culturally expanded purified marrow-derived mesenchymal cells under conditions suitable for differentiating the cells into the type of skeletal or connective tissue needed for implantation.

In an additional aspect, the present invention concerns various methods and devices for using the purified marrow-derived mesenchymal cells in order to enhance the production of hemopoietic cells. For example, one of the embodiments of the present invention is directed to a method for using composite grafts of purified marrow-derived mesenchymal cells to augment the rate of hemopoietic cell rescue during bone marrow transplantation. A further embodiment of the invention concerns a method for using composite grafts of purified marrow-derived mesenchymal cells and ceramics which are implanted into hosts in order to act as catalysts for the production of an ectopic reservoir of hemopoietic stem cells.

DESCRIPTION OF THE DRAWINGS

The following is a brief description of the drawings which are presented for the purposes of illustrating the invention and not for the purposes of limiting the same.

FIG. 2 is a series of photomicrographs (Mallory Heidehain Staining) of a histological section of a composite containing cultured human marrow fibroblasts and ceramic after two weeks of incubation in a nude mouse.

FIG. 3 is a series of photomicrographs (Mallory Heidehian staining) of a histological section of a composite containing cultured human marrow fibroblasts in ceramic after three weeks of incubation in a nude mouse.

FIG. 4 is two photomicrographs (Mallory Heidenhain staining) of a histological section of cultured human marrow fibroblasts in ceramic after six weeks of incubation in a nude mouse.

DETAILED DESCRIPTION OF THE INVENTION

Figure 1:
FIG. 1 is a phase contrast photomicrograph of a monolayer culture of fibroblast-like cells derived from human marrow (100×)

The present invention is derived from the discovery that through a fairly detailed process, the progenitor cells to the various types of connective tissues can be isolated and purified from tissue such as bone marrow. These cells are referred to as "marrow-derived mesenchymal cells" by the present inventors. In this regard, it has been found that although the progenitor marrow-derived mesenchymal cells (i.e. the mesenchymal stem cells) are normally present in bone marrow in very minute amounts and that these amounts greatly decrease with age (i.e. from about 1/10,000 cells in a relatively young patient to about 1/1,000,000 in an elderly patient), the progenitor cells (i.e. the mesenchymal stem cells) can be isolated from tissue and purified when cultured in a specific medium by their selective attachment to substrates. As stated above, this discovery is the subject matter of a co-pending U.S. patent application.

It has also been found that the isolated and purified marrow-derived mesenchymal cells can be grown in an undifferentiated state through mitotic expansion in a specific medium. These cells can then be harvested and activated to differentiate into bone, cartilage, and various other types of connective tissue by a number of factors, including mechanical, cellular, and biochemical stimuli. As a result, it has been determined that the marrow-derived mesenchymal cells possess the potential to differentiate into cells which produce various types of connective tissue, such as osteoblasts and chondrocytes, and possibly tendon, ligament and dermis, and that this potential is retained after isolation and for several population expansions in culture. Thus, by being able to isolate, purify, greatly multiply, and then activate the marrow-derived mesenchymal cells to differentiate into the specific types of connective tissue desired, such as bone-forming osteoblast cells, etc., a highly effective process exists for treating skeletal and other connective tissue disorders.

More particularly, bone marrow is the soft tissue occupying the medullary cavities of long bones, some haversian canals, and spaces between trabecular of cancellous or spongy bone. Bone marrow is of two types—red, which is found in all bones in early life and in restricted locations in adulthood (i.e. in the spongy bone) and is concerned with the production of blood cells (i.e. hemopoiesis) and hemoglobin (thus, the red color); and yellow, which consists largely of fat cells (thus, the yellow color) and connective tissue.

As a whole, bone marrow is a complex tissue comprised of red and white blood cells, their precursors, and a group of cells consisting of fibroblasts, reticulocytes, adipocytes, and endothelial cells which formulate a connective tissue network called "stroma". Cells from the stroma morphologically regulate the differentiation of hemopoietic cells through direct interaction via cell surface proteins and the secretion of growth factors and are involved in the foundation and support of the bone structure. Studies using animal models have suggested that bone marrow contains "prestromal" cells which have the capacity to differentiate into cartilage, bone, and other connective tissue cells. (Beresford, J. N.: Osteogenic Stem Cells and the Stromal System of Bone and Marrow, *Clin. Orthop.*, 240:270, 1989). Recent evidence indicates that these cells, called pluripotent stromal stem cells or mesenchymal stem cells, have the ability to generate into several different types of cell lines (i.e. osteocytes, chondocytes, adipocytes, etc.) upon activation. However, the mesenchymal stem cells are present in the tissue not only in very minute amounts with a wide variety of other cells (i.e. erythrocytes, platelets, neutrophils, lymphocytes, monocytes, cosimophils, basophils, adipose cells, etc.) in an inverse relationship with age, they are capable of differentiating into an assortment of connective tissues depending upon the influence of a number of bioactive factors.

As a result, a critical aspect of the present invention is directed to the discovery of a process of isolating and purifying the marrow-derived mesenchymal cells from tissue prior to differentiation and then culturally expanding the marrow-derived mesenchymal cells to produce a valuable tool for skeletal therapy. The objective of such manipulation is to greatly increase the number of potentially reparative cells and to utilize these cells to redirect and/or reinforce the body's normal reparative capacity. In this regard, the marrow-derived mesenchymal cells can then be subsequently harvested in great numbers and applied to areas of connective tissue damage to enhance or stimulate in-vivo growth for regeneration and/or repair, to improve implant adhesion to various prosthetic devices through subsequent activation and differentiation, enhance hemopoietic cell production, etc.

Along these lines, various procedures are contemplated by the inventors for transferring, immobilizing, and activating the culturally expanded, purified marrow-derived mesenchymal cells at the site for repair, implantation, etc., including injecting the cells at the site of a skeletal defect, incubating the cells with a prosthesis and implanting the prosthesis, etc. Thus, by isolating, purifying and greatly expanding the number of cells prior to differentiation and then actively controlling the differentiation process, the culturally expanded undifferentiated marrow-derived mesenchymal cells can be utilized for various therapeutic purposes such as to elucidate cellular, molecular, and genetic disorders in a wide number of metabolic bone diseases and skeletal dysplasias.

As more specifically indicated below in Example 1, the marrow-derived mesenchymal cells isolated and purified in the present invention were derived from bone marrow attained from a number of different sources, including plugs of femoral head cancellous bone pieces obtained from patients with degenerative joint disease during hip or knee replacement surgery, and from aspirated marrow obtained from normal donors and oncology patients who have marrow harvested for future bone marrow transplantation. Although the harvested marrow was prepared for cell culture separation by a number of different mechanical isolation processes depending upon the source of the harvested marrow (i.e. the presence of bone chips, peripheral blood etc.), the critical step involved in the isolation processes was the use of a specially prepared medium which contained agents which allowed for not only marrow-derived mesenchymal cell growth without differentiation but also for the direct adherence of only the marrow-derived mesenchymal cells to the plastic or glass surface area of the culture dish. By producing a medium which allowed for the selective attachment of the desired marrow-derived mesenchymal cells which were present in the marrow samples in very minute amounts, it was possible to separate the mesenchymal stem cells from the other cells (i.e. red and white blood cells, etc.) present in the bone marrow.

In this regard, it was found that a medium consisting of BGJ$_b$ medium (Gibco, Grand Island, N.Y.) with tested and selected lots of 10% fetal bovine serum (J. R. Scientific, Woodland, Calif., or other suppliers) was well suited for use in the present invention. This medium, which was called "complete medium", contained factors which stimulated marrow-derived mesenchymal cell growth without differentiation and allowed for the selective attachment through specific protein binding sites, etc. of only the marrow-derived mesenchymal cells to the plastic surfaces of Petri dishes. Although the specific operating mechanism of the complete medium for producing the differential attachment is currently not well understood, research is continuing in this area.

The principal components of the BGJ$_b$ Medium (Fitton-Jackson Modification) utilized to formulate the complete medium are set forth below:

| BGJ$_b$ Medium (Fitton-Jackson Modification) | |
|---|---|
| Liquid Component | 320-2591 1X (mg/L) |
| Inorganic Salts: | |
| NaH$_2$PO$_4$.H$_2$O | 90.00 |
| MgSO$_4$.7H$_2$O | 200.00 |
| KCl | 400.00 |
| KH$_2$PO$_4$ | 160.00 |
| NaHCO$_3$ | 3500.00 |
| NaCl | 5300.00 |
| Other Components: | |
| Calcium Lactate | 550.00 |
| D-Glucose | 10000.00 |
| Phenol red | 20.00 |
| Sodium acetate | 50.00 |
| Amino Acids: | |
| L-Alanine | 250.00 |
| L-Arginine | 175.00 |
| L-Arginine HCl | — |
| L-Aspartic acid | 150.00 |
| L-Cysteine HCl.H$_2$O | 101.00 |
| L-Glutamine | 200.00 |
| Glycine | 800.00 |
| L-Histidine | 150.00 |
| L-Histidine HCl.H$_2$O | — |
| L-Isoleucine | 30.00 |
| L-Leucine | 50.00 |
| L-Lysine | 240.00 |
| L-Lysine HCl | — |
| L-Methionine | 50.00 |
| L-Phenylalanine | 50.00 |
| L-Proline | 400.00 |
| L-Serine | 200.00 |
| L-Threonine | 75.00 |
| L-Tryptophan | 40.00 |
| L-Tyrosine | 40.00 |
| DL-Valine | 65.00 |
| L-Valine | — |
| Vitamins: | |
| α-tocopherol phosphate (disodium salt) | 1.00 |
| Ascorbic acid | 50.00 |
| Biotin | 0.20 |
| D-Ca pantothenate | 0.20 |
| Choline chloride | 50.00 |
| Folic acid | 0.20 |
| i-Inositol | 0.20 |
| Nicotinamide | 20.00 |
| Para-aminobenzoic acid | 2.00 |
| Pyridoxal phosphate | 0.20 |
| Riboflavin | 0.20 |
| Thiamine HCl | 4.00 |
| Vitamin B$_{12}$ | 0.04 |

In addition, it was also found that the medium F-12 Nutrient Mixture (Ham) (Gibco, Grand Island, N.Y.) exhibited the desired properties for selective marrow-derived mesenchymal cell separation. The principal components of the F-12 Nutrient Mixture (Ham) are as follows:

| | F-12 Nutrient Mixture (Ham) | |
|---|---|---|
| Component | 320-1765 1X Liquid (mg/L) | 430-1700 Powder (mg/L) |
| Inorganic Salts: | | |
| CaCl$_2$ (anhyd.) | — | 33.22 |
| CaCl$_2$.2H$_2$O | 44.00 | — |
| CuSO$_4$.5H$_2$O | 0.00249 | 0.00249 |
| FeSO$_4$.7H$_2$O | 0.834 | 0.834 |
| KCl | 223.60 | 223.60 |
| KH$_2$PO$_4$ | — | — |
| MgCl$_2$ (anhyd.) | — | 57.22 |
| MgCl$_2$.6H$_2$O | 122.00 | — |
| MgSO$_4$ (anhyd.) | — | — |
| MgSO$_4$.7H$_2$O | — | — |
| NaCl | 7599.00 | 7599.00 |
| NaHCO$_3$ | 1176.00 | — |
| Na$_2$HPO$_4$ (anhyd.) | — | 142.04 |
| Na$_2$HPO$_4$.7H$_2$O | 268.00 | — |
| ZnSO$_4$.7H$_2$O | 0.863 | 0.863 |
| Other Components: | | |
| D-Glucose | 1802.00 | 1802.00 |
| Hypoxanthine | 4.10 | — |
| Hypoxanthine (sodium salt) | — | 4.77 |
| Linoleic acid | 0.084 | 0.084 |
| Lipoic acid | 0.21 | 0.21 |
| Phenol red | 1.20 | 1.20 |
| Putrescine 2HCl | 0.161 | 0.161 |
| Sodium pyruvate | 110.00 | 110.00 |
| Thymidine | 0.73 | 0.73 |
| Amino Acids: | | |
| L-Alanine | 8.90 | 8.90 |
| L-Arginine HCl | 211.00 | 211.00 |
| L-Asparagine.H$_2$O | 15.01 | 15.01 |
| L-Aspartic acid | 13.30 | 13.30 |
| L-Cysteine | — | — |
| L-Cysteine HCl.H$_2$O | 35.12 | 35.12 |
| L-Glutamic acid | 14.70 | 14.70 |
| L-Glutamine | 146.00 | 146.00 |
| Glycine | 7.50 | 7.50 |
| L-Histidine HCl.H$_2$O | 20.96 | 20.96 |
| L-Isoleucine | 3.94 | 3.94 |
| L-Leucine | 13.10 | 13.10 |
| L-Lysine HCl | 36.50 | 36.50 |
| L-Methionine | 4.48 | 4.48 |
| L-Phenylalanine | 4.96 | 4.96 |
| L-Proline | 34.50 | 34.50 |
| L-Serine | 10.50 | 10.50 |
| L-Threonine | 11.90 | 11.90 |
| L-Tryptophan | 2.04 | 2.04 |
| L-Tyrosine | 5.40 | — |
| L-Tyrosine (disodium salt) | — | 7.78 |
| L-Valine | 11.70 | 11.70 |

As indicated above, the complete medium can be utilized in a number of different isolation processes depending upon the specific type of initial harvesting processes used in order to prepare the harvested bone marrow for cell culture separation. In this regard, when plugs of cancellous bone marrow were utilized, the marrow was added to the complete medium and vortexed to form a dispersion which was then centrifuged to separate the marrow cells from bone pieces, etc. The marrow cells (consisting predominantly of red and white blood cells, and a very minute amount of mesenchymal stem cells, etc.) were then dissociated into single cells by passing the complete medium containing the marrow cells through syringes fitted with a series of 16, 18, and 20 gauge needles. It is believed that the advantage produced through the utilization of the mechanical separation process, as opposed to any enzymatic separation process, was that the mechanical process produced little cellular change while an enzymatic process could produce cellular damage particularly to the protein binding sites needed for culture adherence and selective separation, and/or to the protein sites needed for the production of monoclonal antibodies specific for said marrow-derived mesenchymal cells. The single cell suspension (which was made up of approximately $50-100 \times 10^6$ nucleated cells) was then subsequently plated in 100 mm dishes for the purpose of selectively separating and/or isolating the marrow-derived mesenchymal cells from the remaining cells found in the suspension.

When aspirated marrow was utilized as the source of the marrow-derived mesenchymal cells, the marrow stem cells (which contained little or no bone chips but a great deal of blood) were added to the complete medium and fractionated with Percoll (Sigma, St. Louis, Mo.) gradients more particularly described below in Example 1. The Percoll gradients separated a large percentage of the red blood cells and the mononucleate hemopoietic cells from the low density platelet fraction which contained the marrow-derived mesenchymal stem cells. In this regard, the platelet fraction, which contained approximately $30-50 \times 10^6$ cells was made up of an undetermined amount of platelet cells, $30-50 \times 10^6$ nucleated cells, and only about 50-500 marrow-derived mesenchymal cells depending upon the age of the marrow donor. The low density platelet fraction was then plated in the Petri dish for selective separation based upon cell adherence.

In this regard, the marrow cells obtained from either the cancellous bone or iliac aspirate (i.e. the primary cultures) were grown in complete medium and allowed to adhere to the surface of the Petri dishes for one to seven days according to the conditions set forth in Example 1 below. Since no increase in cell attachment was observed after the third day, three days was chosen as the standard length of time at which the non-adherent cells were removed from the cultures by replacing the original complete medium with fresh complete medium. Subsequent medium changes were performed every four days until the culture dishes became confluent which normally required 14-21 days. This represented $10^3-10^4$ fold increase in undifferentiated mesenchymal stem cells.

The cells were then detached from the culture dishes utilizing a releasing agent such as trypsin with EDTA (ethylene diaminetetra-acetic acid) (0.25% trysin, 1 mM EDTA (1X), Gibco, Grand Island, N.Y.) or a chelating agent such as EGTA (ethylene glycol-bis-(2-amino ethyl ether) N,N'-tetraacetic acid, Sigma Chemical Co., St. Louis, Mo.). The advantage produced through the use of a chelating agent over trypsin was that trypsin could possibly cleave off a number of the binding proteins of the mesenchymal stem cells. Since these binding proteins contain recognition sites, when monoclonal antibodies were sought to be produced, a chelating agent such as EGTA as opposed to trypsin, was utilized as the releasing agent. The releasing agent was then inactivated and the detached cultured undifferentiated stem cells were washed with complete medium for subsequent use.

In this regard, the bone and cartilage lineage potentials (i.e. osteo-chondrogenic potential) of fresh and expanded marrow-derived mesenchymal cells under the influence of various bioactive factors were determined using two different in-vivo assays in nude mice. See Example 1 below. One assay involved the subcutaneous implantation of porous calcium phosphate ceramics loaded with cultured marrow-derived mesenchymal cells; the other involved peritoneal implantation of diffusion chambers inoculated with cultured marrow-derived mesenchymal cells. Whole marrow and Percoll gradient separated aspirate fractions were also analyzed in these in-vivo assays. Histological evaluation showed bone formation in the ceramics implanted with the cultured mesenchymal stem cells derived from the femoral head and the iliac crest. No cartilage was observed in any of the ceramic grafts. In contrast, the same cells failed to form any bone or cartilage in the diffusion chambers. While whole marrow has now been shown to form bone when placed as a composite graft with ceramics in a subcutaneous site in nude mice, the amount of bone produced is substantially less than that seen when culture-expanded marrow-derived mesenchymal cells are used.

These results indicated that under certain conditions, culturally expanded mesenchymal cells have the ability to differentiate into bone when incubated as a graft in porous calcium phosphate ceramics. Although the internal factors which influence the mesenchymal stem cells to differentiate into bone as opposed to cartilage cells are not well known, it appears that the direct accessibility of the mesenchymal cells to growth and nutrient factors supplied by the vasculature in porous calcium phosphate ceramics, as opposed to the diffusion chamber, influenced the differentiation of the mesenchymal stem cells to bone.

As a result, the isolated and culturally expanded marrow-derived mesenchymal cells can be utilized under certain specific conditions and/or under the influence of certain factors, to differentiate and produce the desired cell phenotype needed for connective tissue repair or regenerative and/or to the implantation of various prosthetic devices. For example, using porous ceramic cubes filled with culture-expanded human marrow-derived mesenchymal stem cells, bone formation inside the pores of the ceramics has been generated after subcutaneous incubations in immunocompatible hosts. In a recent study conducted by the inventor's lab, i.e. Ohgushi, H., Goldberg, V., and Caplan, A. *Acta Scandia.*, 60:334-339, 1989, rat marrow in a composite graft with porous ceramic was used to fill a segmental defect in the femur of the rat. Bone was shown to fill the pores of the ceramic and anchor the ceramic-marrow graft to the host bone.

The following examples are included for the purposes of further illustrating the detailed steps of the present invention.

EXAMPLE 1

The Isolation, Purification and Cultural Expansion of Marrow-Derived Mesenchymal Cells

Marrow Harvest

Marrow in femoral head cancellous bone pieces was obtained from patients with degenerative joint disease during hip or knee joint replacement surgery. In addition, marrow was also obtained by iliac aspirate from normal donors and oncology patients who were having marrow harvested for future bone marrow transplantation. All of the oncology patients had malignancies unrelated to the stromal cells and the stromal cells expressed normal karyotype.

Preparation of Marrow for Cell Culture

A. From Plugs of Cancellous Bone Marrow

Plugs of cancellous bone marrow (0.5-1.5 ml) were transferred to sterile tubes to which 25 ml $BGJ_b$ medium (GIBCO, Grand Island, N.Y.) with selected batches of 10% fetal bovine serum (JR Scientific, Woodland, Calif.) (complete medium) was added. The tubes were vortexed to disperse the marrow then spun at 1000× g for 5 minutes to pellet cells and bone pieces. The supernatant and fat layer were removed and the marrow and bone were reconstituted in 5 ml complete medium and vortexed to suspend the marrow cells. The suspended cells were collected with a 10 ml syringe fitted with an 16 gauge needle and transferred to separate tubes. Bone pieces were reconstituted in 5 ml. Complete medium and the marrow cells were collected as before. Collection of marrow cells was considered complete when a pellet of yellowish-white cancellous bone pieces was all that remained in the original tube. Marrow cells were separated into a single cell suspension by passing them through syringes filled with 18 and 20 gauge needles. Cells were spun at 1000× RPM for 5 minutes after which the fat layer and supernatant were removed. Cells were reconstituted in complete medium, counted with a hemocytometer (red blood cells were lyzed prior to counting with 4% acetic acid), and plated in 100 mm dishes at $50-100 \times 10^6$ nucleated cells/dish.

B. From Aspirate Bone Marrow

Aspirate marrow (5-10 ml) was transferred to sterile tubes to which 20 ml complete medium was added. The tubes were spun at 1000× RPM for 5 minutes to pellet the cells. The supernatant and fat layer were removed and the cell pellets (2.5-5.0 ml) were loaded onto 70% Percoll (Sigma, St. Louis, Mo.) gradients and spun at 460× g for 15 minutes. The gradients were separated into three fractions with a pipet: top 25% of the gradient (low density cells-platelet fraction), pooled density=1.03 g/ml; middle 50% of the gradient (high density cells-mononucleated cells), pooled density=1.10 g/ml; and, bottom 25% of the gradient (red blood cells), pooled density=1.14 g/ml. In preliminary experiments each of these three pools were plated separately in complete medium in 100 mm dishes. Adherent cells were observed to be localized to the low density cells. To produce adherent cell cultures for all subsequent experiments only the low density cells were plated.

Culturing and Passaging of Marrow Stromal Cells

Marrow cells from either the femoral head cancellous bone or the iliac aspirate were cultured in complete medium (i.e. $BGl_b$ medium with 10% fetal bovine serum) at 37° C. in humidified atmosphere containing 95% air and 5% $CO_2$. In preliminary experiments the cells were allowed to attach for 1, 3, or 7 days prior to the initial medium change. No increase in cell attachment was observed after day 1, therefore one day was chosen as the standard length of time at which nonadherent cells were removed from the cultures by replacing the original medium with 7 ml of fresh complete medium. Subsequent medium changes were performed every 4 days. When culture dishes became confluent, the cells were detached with 0.25% trypsin with 0.1 mM EDTA (GIBCO) for 10-15 minutes at 37° C. The action of trypsin was stopped with ½ volume fetal bovine serum. The cells were counted, split 1:3, and replated in 7 ml complete medium. Aliquots of cells were cryopreserved in 90% fetal bovine serum with 10% DMSO (freezing medium).

Preparation of Cultures for In Vivo Incubations in Ceramics and Diffusion Chambers Cultured cells were detached from plates as described for subculturing. After inactivating the trypsin, the cells were washed twice with 10 ml serumless $BGJ_b$ medium, counted, and then adjusted to the appropriate concentration with serumless $BGJ_b$. Whole marrow and Percoll fractions were rinsed twice with 10 ml serumless $BGJ_b$ and adjusted to the appropriate concentration with serumless $BGJ_b$. Porous ceramic cubes (3 mm³) composed of 60% hydroxyapatite+40% β-tricalcium phosphate (Zimmer Corporation, Warsaw, Ind.) were added to the cell suspensions under slight vacuum and soaked for up to 90 minutes prior to surgical implantation.

Diffusion chambers were constructed of lucite rings and Millipore filters as described elsewhere (Ashton, et al., 1980). Cells were prepared as described above and added to the chambers in 100-140 ul of serumless $BGJ_b$ medium. Chambers were sealed with a drop of cement and immersed in serumless $BGJ_b$ for up to 90 minutes prior to surgical implantation.

Surgical Implantation of Ceramics and Diffusion Chambers

Ceramics—Nude mice (National Institute of Health, nu/nu strain) were anesthetized with ether and placed on their stomachs. Four small longitudinal incisions (5 mm) were made along the backs. Ceramic-marrow grafts were inserted into the pockets and positioned as lateral in the pockets as possible. Incisions were closed with Autoclips (Becton Dickenson and Company, Parsippany, N.J.). Each pair of pockets received a different pair of ceramic-marrow graft so that four different samples (2 ceramic cubes per sample) were incubated per mouse.

Diffusion Chambers—Nude mice were anesthetized with ether and placed on their backs. Incisions were made through the skin and peritoneum, and diffusion chambers were inserted into the peritoneal cavity. The peritonea were closed with sutures and the skin, with Autoclips. Only one chamber was inserted per mouse and it contained cultured cells identical to cells loaded in one of the four pairs of the ceramic-marrow grafts implanted into the same mouse.

Histological Evaluation

Nude mice were sacrificed and the ceramic-marrow grafts harvested 1-8 weeks after implantation (Table 1 and Table 3). Ceramic were fixed in 10% buffered formalin, demineralized for 7 hours in RDO Rapid Bone Decalcifier (Dupage Kinetics Laboratories, Inc., Plainfield, Ill.), embedded in paraffin, serial sectioned (5 um thick), and stained with Mallory Heidenhain or Toluidine blue.

Diffusion chambers were harvested 3-10 weeks after implantation (Table 2 and Table 3). Chambers were fixed in 10% buffered formalin, paraffin embedded, serially sectioned, and stained with Mallory Heidenhain or Toluidine blue.

TABLE 1

Incubation of Composite Graphs of Cultured Human Marrow Cells and Ceramic in Nude Mouse

| Donor # | Age/Sex | Site | Pass # | Conc. | Weeks Postimplantation 1 | 2 | 3 | 4 | 5 | 6 | 7 | 8 |
|---|---|---|---|---|---|---|---|---|---|---|---|---|
| 1 | 50/M | FH | 4 | $20 \times 10^6$ | | | | | | + | | |
| 1 | 50/M | FH | 5 | $2 \times 10^6$ | | | − | | + | + | | |
| 1 | 50/M | FH | 6 | $0.7 \times 10^6$ | | | + | + | | | | + |
| 2 | 65/M | FH | 1 | $5 \times 10^6$ | | | | | ++ | +++ | | |
| 2 | 65/M | FH | 2 | $4 \times 10^6$ | | | +++ | | | +++ | | +++ |
| 3 | 65/M | FH | P | $6 \times 10^6$ | − | + | | | | +++ | +++ | +++ |
| 4 | 66/F | FH | 1 | $10 \times 10^6$ | | | + | | +++ | +++ | | +++ |
| 5 | 64/M | FH | P | $8 \times 10^6$ | − | + | ++ | | | +++ | | +++ |
| 6 | 64/M | FH | 1 | $4 \times 10^6$ | | + | | | | +++ | | +++ |
| 7 | 67/F | FH | P | $7 \times 10^6$ | − | + | ++ | +++ | | | | |
| 8 | 34/F | IC | 1 | $4 \times 10^6$ | | | − | | | + | | |
| 9 | 42/M | IC | P | $4 \times 10^6$ | | | − | | | − | | |
| 10 | 38/M | IC | P | $4 \times 10^6$ | | | − | | | ++ | | |
| 11 | 45/M | IC | P | $4 \times 10^6$ | | | + | | | ++ | | |

Pass # is the number of subcultures
Conc. is the concentration of cells in cells/ml
Site is the site of marrow harvest
FH - femoral head
IC - Iliac crest
P - primary cultures
− = None of the pores contained bone
+ = 0–30% of the pores contained bone
++ = 30–70% of the pores contained bone
+++ = greater than 70% of the pores contained bone

TABLE 2

Incubation of Cultured Human Marrow Cells in Diffusion Chambers

| Donor | Age/Sex | Site | Pass # | Cells/Chamber | 3 | 6 | 8 | 10 |
|---|---|---|---|---|---|---|---|---|
| 1 | 50/M | FH | 4 | $4 \times 10^6$ | | | − | |
| 2 | 65/M | FH | 1 | $3 \times 10^6$ | | | − | |
| 3 | 65/F | FH | P | $4 \times 10^6$ | | − | − | |
| 4 | 66/F | FH | 1 | $4 \times 10^6$ | − | | | − |
| 5 | 64/M | FH | P | $4.5 \times 10^6$ | | − | | |

P = primary culture
Pass # = the number of subcultures
Site = the site of marrow harvest
FH = femoral head
IC = iliac crest
− = no bone in chamber
+ = 0–30% of chamber contains bone
++ = 30–70% of chamber contains bone
+++ = more than 70% of chamber contains bone

RESULTS

In Vitro Cultures

Adherent marrow-derived mesenchymal cells from femoral head cancellous bone or iliac aspirate have similar morphology, almost all being fibroblastic, with few adipocytic, polygonal or round cells (FIG. 1). Histochemical staining for alkaline phosphatase yields variable positive reactivity with no noticeable difference between cells derived from cancellous bone marrow or aspirate marrow. Adherent cells from both harvest sites fail to produce an extracellular matrix which stains metchromatically with Toluidine blue or positive for von Kossa; a positive staining would have indicated the possibility that cartilage or bone tissue was produced in these cultures.

In Vivo Incubation of Cultured Marrow Cells with Ceramics

Calcium phosphate ceramic blocks were soaked in culture medium containing various concentrations of cultured marrow-derived mesenchymal cells from either femoral head cancellous bone or iliac aspirate. The marrow donors included both males and females ranging in age from 34 to 67 years old (Table 1). Cells from primary culture and first through sixth passage were assayed, with the cell-loading concentration ranging from $0.7 \times 10^6$ to $20 \times 10^6$ cells/ml. Marrow-derived mesenchymal cell-loaded ceramic blocks were surgically implanted subcutaneously into nude mice and incubated from 1 to 8 weeks. Upon harvest, ceramics were fixed, demineralized and the presence of bone and cartilage was determined by histological evaluation. Table 1 summarizes the data.

Figure 2A:
FIG. 2A shows the formation of new bone (b) lining the pores of the ceramic ghost (c) (40×)
Figure 2B:
FIG. 2B indicates that the fibrous tissue (f) was present in most of the pores (100× of boxed area in FIG. 2A)
Figure 2C:
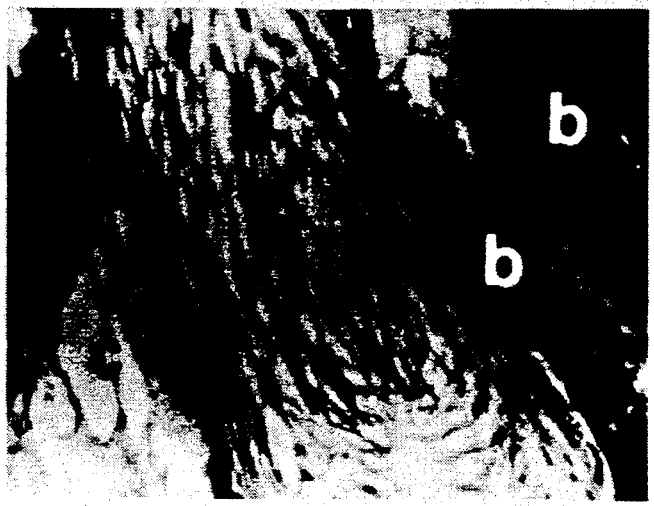
FIG. 2C indicates that the osteocytes (o) were clearly visible embedded within the bone matrix (400× of boxed area in FIG. 2B)
Figure 3B:
FIG. 3B demonstrates that the fibrous tissue (f) still remained in the inner spaces of most of the pores. In addition, host vascular (v) was also present in some pores (100× of boxed area in FIG. 3A)
Figure 3A:
FIG. 3A indicates that bone (b) was observed lining a greater number of pores of the ceramic ghost (c) than in FIG. 2 (2 week incubation) (40×)
Figures 4A, 4B:
FIG. 4A indicates that bone (b) was observed lining most of the pores of the ceramic ghost (c) (40×)
FIG. 4B shows the fibrous tissue (f) observed in the inner spaces of a few pores, however, marrow (m) has replaced the fibrous tissue in a majority of the pores (100× of the boxed area in FIG. 4A).

Bone, but not cartilage, was observed in the pores of each graft of ceramics and cultured marrow-derived mesenchymal cells from femoral head cancellous bone. The earliest bone was observed at 2 weeks in less than 30% of the pores of each ceramic (FIG. 2). At three weeks, the number of pores containing bone varied from less than 30% to greater than 70% (FIG. 3). By six weeks, the majority of the ceramics contained bone in greater than 70% of the pores (FIG. 4). No obvious correlation could be made between the age of the donors and the amount of bone formation. In contrast, passage number appeared to have some influence on the amount of bone formation, with primary cultures and early passaged cells (1st–2nd passages) giving more bone formation than late passaged cells (4th–6th passages). Bone formation appears to begin with osteoblast differentiation and bone deposition onto the surfaces of the ceramic pores and appears to progress towards the center of the pores as cells lining the surface of the new bone matrix secrete osteoid on top of previously deposited matrix. Maintenance of ceramic marrow-derived mesenchymal cell grafts for periods of 6–8 weeks resulted in bone remodeling and the identification of marrow elements in the inner spaces of each pore (FIG. 2C).

Grafts of ceramics and cultured marrow-derived mesenchymal cells from iliac aspirate produced bone in three of the four samples tested (Table 1). Cartilage was not observed in any of the grafts. Bone formation in the three positive grafts was less than that observed from ceramics grafted with cultured cells from femoral head cancellous bone marrow. Less than 30% of the pores contained bone at 3 weeks and 30–70% of the pores contained bone at 6 weeks. The remainder of the pores contained fibrous tissue and vasculature of, in all likelihood, host origin.

In Vivo Incubation of Cultured Marrow Cells in Diffusion Chambers

The osteo-chondrogenic potential of cultured marrow-derived mesenchymal cells was also assayed by loading cells in diffusion chambers and surgically implanting them intraperitonelly into nude mice. The cells were obtained from the same cultures used in the ceramic assays (Table 2), and the diffusion chambers were implanted into the peritonea of the same nude mice which received subcutaneous ceramic-marrow-derived mesenchymal cell grafts. After incubations for 3–10 weeks, the chambers were harvested and the presence of bone and cartilage formation determined by histological evaluation. In contrast to the presence of bone in grafts of ceramic and cultured cells from cancellous bone, no bone or cartilage was observed in any of the diffusion chambers containing cultured cancellous bone marrow-derived mesenchymal cells even after 10 weeks incubation (Table 2). Cultured iliac aspirate marrow-derived mesenchymal cells also failed to produce bone or cartilage in the diffusion chambers. Instead, hypocellular sparse fibrous tissue was observed in most of the chambers.

Discussion

In this example, human marrow-derived mesenchymal cells were shown to reproducibly exhibit osteogenic potential following their mitotic expansion in culture when assayed in porous calcium phosphate ceramics in nude mice. Osteogenesis was not observed when the same cells were incubated in diffusion chambers in the same nude mice. Collectively, these data show that human marrow contains cells, which can be selected and expanded in culture, which have the potential to differentiate into bone when incubated in vivo as a graft in porous calcium phosphate ceramics.

The absence of bone formation in diffusion chambers suggests that the ceramics assay may be a more sensitive assay for differentiation of bone from marrow cells. Bab, et al. (Bab, I., Passi-Even, L., Gazit, D., Sekeles, E., Ashton, B. A., Peylan-Ramu, N., Ziv, I., and Ulmansky, M.; Osteogenesis in vivo diffusion chamber cultures of human marrow cells, *Bone and Mineral* 4; 373, 1988) observed bone in four of eight diffusion chambers implanted with human marrow from two child donors, however, these authors failed to observe bone when whole marrow from older donors was incubated in diffusion chambers in nude mice. In addition, Davies (Davies, J. E., Human bone marrow cells synthesize collagen, in diffusion chambers, implanted into the normal rat, *Cell. Biol. Int. Rep.* 11, 2:125, 1987) did not observe bone formation in diffusion chambers inoculated with fresh marrow from a five year old female, nor was bone formation observed by Ashton, et al. (Ashton, B. A., Cave, F. A., Williamson, M., Sykes, B. C., Couch, M., and Poser, J. W.; Characterization of cells with high alkaline phosphates activity derived from human bone and marrow; preliminary assessment of their osteogenicity, *Bone*, 5:313-319, 1985) in diffusion chambers inoculated with cultured fibroblasts from composite pieces of bone and marrow from children and young adults.

In the present example, bone formation was not observed in diffusion chambers inoculated with cultured marrow-derived mesenchymal cells from several older donors. However, bone formation was observed in ceramic filled grafts with cultured marrow-derived mesenchymal cells from the same preparations of older donors (34–67 years old) which failed to generate bone in diffusion chambers. The factors which apparently make ceramics a more sensitive vehicle for bone differentiation from marrow-derived mesenchymal cells are unclear, but may involve direct accessibility of the marrow-derived mesenchymal cells to growth and nutrient factors supplied by the vasculature or direct interaction with vascular cells which are limited because of diffusion chamber geometry (Jaroma, H. J., and Rotsila, V. A., Effect of diffusion chamber pore size on differentiation and proliferation of periosteal cells, *Clin. Orthop.*, 236, 258, 1988) (Villanueva, J. E., and Nimni, M. E., Promotion of calvarial cell osteogenesis by endothelial cells in diffusion chambers, *J. Cell. Biol.*, 109, 4, part. 2:42a (abstract).

The question of origin of the bone formed in the ceramic pores is important since the donor marrow-derived mesenchymal cells are not physically separated from the host cells as is the case for diffusion chambers. Recent data by Goshima, et al. (Jun Goshima, Victor M. Goldberg and Arnold I. Caplan, "The Origin of Bone Formed in Composite Grafts of Porous Calcium Phosphate Ceramic and Marrow Cells" (1988) Submitted) indicate that bone formation in ceramic grafts is a biphasic phenomenon with the initial bone formation being of donor origin. When this donor-derived bone has partially filled the pores of the ceramics, host-derived cells begin remodeling the donor bone, thus beginning the second phase of host-derived bone formation. Eventually, a marrow cavity forms in the center, with a cocoon of host-derived bone which has been laid on the partially remodeled inner surfaces of original donor bone. To confirm the origin of the bone formed with human marrow, the present inventors are currently assaying ceramic grafts with species-specific monoclonal antibodies directed against human osteocytes. The preliminary data shows antibody reactivity to the osteocytes within the grafts, thus suggesting that the bone formed in the porous ceramic is of human and not mouse origin.

Cultured marrow-derived mesenchymal cells originating from femoral head cancellous bone appear to be more osteogenic than cultured marrow-derived mesenchymal cells from iliac aspirated marrow; 9 out of 9 cancellous bone marrow samples produced bone in ceramics, whereas, 3 out of 4 aspirated marrow-derived mesenchymal cell samples produced bone in ceramics. In addition, bone was present in fewer pores in ceramics grafted with aspirated marrow-derived mesenchymal cell than ceramics grafted with femoral head marrow-derived mesenchymal cells. The reasons for the differences is unclear, but, may be associated with the proximity of the harvested marrow stromal cells to the bone surface in the original tissue. Ashton, et al. (Ashton, B. A., Eaglesom, C. C., Bab, I., and Owen, M. E., Distribution of fibroblastic colony-forming cells in rabbit bone marrow and assay of their osteogenic potential by an in vivo diffusion chamber method, *Calcif. Tissue Int.*, 36:83, 1984) showed that cultured rabbit marrow stromal cells differ in their colony forming potential in vitro and osteogenic potential in diffusion chambers depending on their original proximity to the endosteal surface. Cells closest to the endosteal surface were shown to have four times the colony forming efficiency as compared to cells of the core. In the present study, marrow from cancellous bone was harvested by vigorous vortexing to separate the cancellous bone from the marrow cells. This likely produces a population of marrow enriched in cells derived from near the endosteal surface, as compared to aspirate marrow where vigorous separation of marrow cells from cancellous bone is not possible. The inventors observed a consistently higher initial number of adherent cells from cancellous bone marrow as compared to aspirate marrow, which is similar to the observations of Ashton, et al. (Ashton, B. A., Eaglesom, C. C., Bab, I., and Owen, M. E., Distribution of fibroblastic colony-forming cells in rabbit bone marrow and assay of their osteogenic potential by an in vivo diffusion chamber method, *Calcif. Tissue Int.*, 36:83, 1984).

In the case of marrow from adult donors, cartilage was not observed in this study or the study by Bab, et al. (Bab, I., Passi-Even, L., Gazit, D., Sekeles, E., Ashton, B. A., Peylan-Ramu, N., Ziv, I., and Ulmansky, M.; Osteogenesis in in vivo diffusion chamber cultures of human marrow cells, *Bone and Mineral* 4; 373, 1988). It may be that there is an age-dependent determination of marrow-derived cells for the osteogenic lineage over the chondrogenic lineage. Alternatively, culturing conditions in the present study may be selective for osteoprogenitor cells over mesenchymal stem cells or may drive mesenchymal stem cells towards the osteogenic lineage prior to in vivo analysis in ceramics. Present studies are being directed towards addressing these possibilities.

The most important realization from the studies set forth in the above example is that the ceramics graft technique provides a sensitive assay for identifying the osteogenic potential of marrow-derived mesenchymal cells. Importantly, such osteogenic cells can be obtained from human donors of a wide age range. These observations indicate that the ex vivo expansion of cells possessing an osteogenic potential may be used for clinical circumstances requiring augmentation of osteogenesis.

EXAMPLE 2

A. Cellular Repair of Skeletal Defects

The culturally expanded marrow-derived mesenchymal cells may also be used to repair skeletal defects which normally do not heal. One class of skeletal defects that can be repaired, is the class of large skeletal defects in bone caused by injury or produced by the removal of large sections of bone infected with tumor. Under normal circumstances, this type of defect does not heal and creates nonunion of the bone. This type of defect may be treated by implanting cultured mesenchymal cells contained in calcium phosphate ceramic vehicles into the defect site. The ceramic will then be osteoconductive to surrounding bone, thereby promoting bony ingrowth along the edges of the ceramic, which will also result in stabilization of the implant in the defect. In addition, the marrow-derived mesenchymal cells will differentiate into osteoblasts, which will then synthesize bone in the ceramic pores. After the cultured cells fill about one third of the pores of the ceramic with bone, applicants expect that the host cells brought in by the vasculature will continue to make bone in the ceramics. Other host cells brought in by the vasculature will then begin to remodel the newly synthesized bone and the ceramic vehicle. Eventually, the defect will become filled with live bone with a marrow cavity in the middle, with the ceramic vehicle becoming completely degraded over time.

A second class of defect that may be repaired by the culture-expanded marrow-derived mesenchymal cells of the present invention, is the damaged articular cartilage generated by trauma or by diseases such as osteoarthritis and rheumatoid arthritis. Under normal circumstances, damage to articular cartilage does not heal, except in very young individuals where the underlying bone is also damaged so that a bloody wound is created. It is projected by the present invention that this type of defect can be treated by implanting cultured marrow-derived mesenchymal cells into the defect. The cells will be formatted in carriers which will hold the cells in the defect, and present them in a manner (round cell morphology) that they differentiate into chondrocytes. In this regard, the applicants envision that a suitable carrier can be constructed of collagen or fibrin, since both have low antigenicity, are pliable to mold to the shape of the defect, and promote round cell shape (which applicants known to be important to induction of chondrocyte differentiation).

B. Anchoring Prothetic Devices

The culturally-expanded marrow-derived mesenchymal cells may also be used to improve the anchoring of prothetic devices used to replace badly damaged joints including the hip, knee, shoulder, elbow and hand. The established method for anchoring these devices is by the use of polymethyl methacrylate cement. Although fairly successful, this method results in a failure rate of about 5-10% due to cement cracking. A second, more recent method of anchoring prothetic devices, is by the use of spaghetti wire which provides a surface for the ingrowth of osteogenic cells. The present invention may be used in conjunction with the spaghetti wire method thereby speeding the process of bony ingrowth. This will be accomplished by coating the prothetic device surfaces with whole marrow or cultured cells prior to implantation. These cells may also be pretreated with growth factors or cytokines to increase the rate of, and the amount of bone formation into the implant. Faster and more complete bony ingrowth should result in stronger, longer lasting implants.

C. Augmentation of Marrow Transplantation

Marrow transplantation has become an increasingly popular treatment for patients with a variety of cancers. Treatment normally begins with the harvesting of marrow from patients during a period of remission. The harvested marrow is cryopreserved and stored until the patient becomes symptomatic, at which time the patient is treated with radiation and chemotherapy and then given back his/her own marrow to reestablish the marrow tissue destroyed during the radiation and chemotherapy treatment. This method is suboptimal because the stroma of the marrow, which is made from mesenchymal cells, is also destroyed by radiation and chemotherapy and is not reestablished prior to transplantation of the marrow hemopoietic cells. Furthermore, intact stroma has previously been shown to be necessary for hemopoietic stem cell differentiation.

An additional embodiment of the invention concerns the use of culture-expanded mesenchymal cells to optimize the marrow transplantation process. At the time of marrow harvest, an aliquot may be taken and introduced into culture. The marrow-derived mesenchymal cells can be isolated, purified and culturally expanded and then cryopreserved until the time of transplantation. The culturally-expanded cells may then be injected into the patient prior to the reintroduction of the whole marrow in order to reestablish the marrow stroma and therefore speed the rate of hemopoiesis. Alternatively, the culturally expanded cells may be added to whole marrow prior to infusion of the whole marrow, to insure the whole marrow contains a sufficient quanta of mesenchymal cells for rapid fabrication of the marrow stroma.

D. Stimulation of Hemopoietic Cell Reservoir

From the procedures described in detail in Example 1, implantation of cultured mesenchymal cells in ceramic blocks results in bone formation inside the pores of the ceramic, followed by establishment of a marrow cavity inside the newly layed bone. The cells that generate the marrow cavity must be supplied by the vasculature of the host, which quickly invades the pores of ceramic blocks within a few hours of being implanted. It is not clearly understood why composite grafts of culture mesenchymal cells and ceramics induce recruitment of hemopoietic stem cells and other marrow elements, however, the fact that this does occur allows for the use of these grafts as a way to sequester hemopoietic stem cells and generate a hemopoietic stem cell reservoir. The reservoir of hemopoietic stem cells can then be used in clinical applications such as marrow transplantation as an alternative method for harvesting hemopoietic stem cells.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method for repairing connective tissue damage comprising:
   a) providing culturally expanded purified human marrow-derived mesenchymal cells which have been isolated from a bone marrow specimen by adding the bone marrow specimen to a medium which contains factors which stimulate mesenchymal stem cell growth without differentiation and allows, when cultured, for selective adherence of only the mesenchymal stem cells to a substrate surface; and,
   b) applying the culturally expanded purified human marrow-derived mesenchymal cells to an area of connective tissue damage under conditions suitable for differentiating the cells into connective tissue cells necessary for repair.

2. The method of claim 1 wherein the culturally expanded purified marrow-derived mesenchymal cells are applied to the area of connective tissue damage by in vivo administration.

3. The method of claim 1 wherein the culturally expanded purified marrow-derived mesenchymal cells are applied to the area of connective tissue damage by injection.

4. The method of claim 1, further comprising the step of adding to said mesenchymal stem cells a factor which stimulates differentiation of the marrow-derived mesenchymal cells into osteocytes.

5. A method for enhancing implantation of a prosthetic device in connective tissue comprising:
   a) providing culturally expanded purified human marrow-derived mesenchymal cells which have been isolated from a bone marrow specimen by adding the bone marrow specimen to a medium which contains factors which stimulate mesenchymal stem cell growth without differentiation and allows, when cultured, for selective adherence of only the mesenchymal stem cells to a substrate surface;
   b) adhering said culturally expanded purified human marrow-derived mesenchymal cells on to a prosthetic device; and,
   c) implanting the prosthetic device containing the culturally expanded purified marrow-derived mesenchymal cells under conditions suitable for differentiating the cells into connective tissue.

6. The method of claim 5 further comprising the steps of adding to said marrow-derived mesenchymal cells a factor which stimulates differentiation of the marrow-derived mesenchymal cells into osteocytes.

7. A method for repairing connective tissue damage comprising the steps of:
   a) providing a bone marrow specimen containing human mesenchymal stem cells and bone pieces;
   b) adding the bone marrow specimen to a medium which contains factors which stimulate mesenchymal stem cell growth without differentiation and allows, when cultured, for the selective adherence of only the mesenchymal stem cells to a substrate surface;
   c) separating the bone pieces from the bone marrow medium mixture;
   d) dissociating the marrow cells into single cells;
   e) culturing the dissociated marrow cells in the bone marrow medium mixture;
   f) separating the non-adherent matter from the substrate surface thereby producing isolated culturally expanded mesenchymal stem cells; and,
   g) applying the culturally expanded purified mesenchymal stem cells to the area of connective tissue damage under conditions suitable for differentiating the cells into the type of connective tissue cells necessary for repair.

8. The method of claim 7 wherein the culturally expanded purified mesenchymal stem cells are applied to the area of connective tissue damage by in vivo administration.

9. The method of claim 7 wherein the culturally expanded purified mesenchymal stem cells are applied to the area of connective tissue damage by injection.

10. The method of claim 7 further comprising the step of adding to said mesenchymal stem cells a factor which stimulates differentiation of the mesenchymal stem cells into osteocytes.

11. The method of claim 7 wherein said medium is comprised of $BGJ_b$ medium with 10% fetal bovine serum.

12. The method of claim 7 wherein said medium is comprised of F-12 nutrient mixture.

13. A method for enhancing implantation of a prosthetic device in a connective tissue comprising:
   a) providing a bone marrow specimen containing human mesenchymal stem cells and bone pieces;
   b) adding the bone marrow specimen to a medium which contains factors which stimulate mesenchymal stem cell growth without differentiation and allows, when cultured, for selective adherence of only the mesenchymal stem cells to a substrate surface;

c) separating the bone pieces from the bone marrow medium mixture;

d) dissociating the marrow cells into single cells;

e) culturing the dissociated marrow cells in the bone marrow medium mixture;

f) separating non-adherent matter from the substrate surface thereby producing isolated culturally expanded mesenchymal stem cells;

g) adhering said culturally expanded purified mesenchymal stem cells on to a prosthetic device; and, h) implanting the prosthetic device containing the culturally expanded purified mesenchymal stem cells under conditions suitable for differentiating the cells into skeletal tissue.

14. The method of claim 13, further comprising the steps of adding to said mesenchymal stem cells a factor which stimulates differentiation of the mesenchymal stem cells into osteocytes.

15. The method of claim 13, wherein said medium is comprised of $BGJ_b$ medium with 10% fetal bovine serum.

16. The method of claim 13, wherein said medium is comprised of F-12 nutrient mixture.

17. A method for generating a hematopoietic stem cell reserve comprising:

a) providing human marrow-derived mesenchymal stem cells that have been isolated, purified and culturally expanded;

b) applying the isolated, purified and culturally expanded marrow-derived human mesenchymal stem cells to a porous carrier;

c) implanting the porous carrier containing the mesenchymal stem cells into a host patient;

d) allowing for a sufficient period of time for inducement of hematopoietic stem cells present in the host patient into the porous carrier; and e) harvesting the hematopoietic stem cells present in the porous carrier.

18. The method of claim 17, wherein said porous carrier comprises about 60% hydroxyapatite and about 40% tricalcium phosphate.

19. A method for generating a human hematopoietic stem cell reserve comprising:

a) providing a bone marrow specimen containing human marrow-derived mesenchymal stem cells and bone pieces;

b) adding the bone marrow specimen to a medium which contains factors which stimulate the human marrow-derived mesenchymal stem cells to grow without differentiation and allows, when cultured, for selective adherence of only the marrow-derived human mesenchymal stem cells to a substrate surface;

c) separating the bone pieces from the bone marrow medium mixture;

d) dissociating the marrow cells into single cells;

e) culturing the dissociated marrow cells in the bone marrow medium mixture;

f) separating non-adherent matter from the substrate surface, thereby producing isolated culturally expanded human marrow-derived mesenchymal stem cells;

g) applying the culturally expanded human marrow-derived mesenchymal stem cells to a porous carrier;

h) implanting the porous carrier containing the culturally expanded marrow-derived mesenchymal cells into a host patient;

i) allowing for a sufficient period of time for inducement of hematopoietic stem cells present in the host patient into the porous carrier; and, j) harvesting the hematopoietic stem cells collected by the porous carrier.

20. The method of claim 19, wherein said porous carrier is comprised of about 60% hydroxyapatite and about 40% tricalcium phosphate.

21. The method of claim 19, wherein said medium is comprised of $BGJ_b$ Medium with 10% fetal bovine serum.

22. The method of claim 19, wherein said medium is comprised of F-12 Nutrient Mixture.

23. A method for repairing connective tissue damage comprising:

a) providing a bone marrow specimen containing human mesenchymal stem cells;

b) adding the bone marrow specimen to a medium thereby producing a bone marrow specimen-medium mixture, wherein said medium contains factors that stimulate mesenchymal stem cell growth without differentiation and allows, when cultured, for selective adherence of only the mesenchymal stem cells to a substrate surface;

c) adding the bone marrow specimen-medium mixture to a density gradient which separates cells into low, medium and high density cell fractions based on differences in density;

d) removing the low density cell fraction from the density gradient;

e) adding the low density cell fraction to the medium used in step (b) to produce a low density cell fraction-medium mixture;

f) culturing the low density cell fraction-medium mixture, thereby selectively adhering only the mesenchymal stem cells to the substrate surface;

g) removing any non-adherent matter from substrate surface;

h) removing the remaining adherent mesenchymal stem cells from the substrate surface with a releasing agent, thereby allowing for the isolated mesenchymal stem cells to be recovered; and, i) applying an culturally expanded purified human marrow-derived mesenchymal cells to the area of connective tissue damage under conditions suitable for differentiating the cells into connective tissue necessary for repair.

* * * * *

UNITED STATES PATENT AND TRADEMARK OFFICE
CERTIFICATE OF CORRECTION

PATENT NO. : 5,226,914
DATED : July 13, 1993
INVENTOR(S) : Arnold I. Caplan, et al.

It is certified that error appears in the above-indentified patent and that said Letters Patent is hereby corrected as shown below:

Column 1, insert before the first paragraph between Lines 5 and 6:

-- The United States Government has rights to this invention pursuant to a contract granted by the National Institutes of Health Grant No. AR-37726 awarded to Case Western Reserve University. --

Signed and Sealed this

Thirty-first Day of May, 1994

Attest:

BRUCE LEHMAN

Attesting Officer

Commissioner of Patents and Trademarks